United States Patent [19]
Roberts et al.

[11] Patent Number: 6,156,935
[45] Date of Patent: Dec. 5, 2000

[54] CHIRAL PHOSPHORUS-BASED LIGANDS

[75] Inventors: Stanley Michael Roberts, Liverpool; Christopher Palmer; Ulrich Berens, both of Cambridge, all of United Kingdom

[73] Assignee: Chirotech Technology, Ltd., United Kingdom

[21] Appl. No.: 09/086,657

[22] Filed: May 29, 1998

[30] Foreign Application Priority Data

May 30, 1997 [GB] United Kingdom .................... 9711201
Jun. 5, 1997 [GB] United Kingdom .................... 9711670
Feb. 12, 1998 [GB] United Kingdom .................... 9803022

[51] Int. Cl.$^7$ ................. C07F 9/02; C07C 35/28
[52] U.S. Cl. ................. 568/14; 568/15; 568/819
[58] Field of Search ................. 568/10, 11, 12, 568/16, 14, 15, 819

[56] References Cited

U.S. PATENT DOCUMENTS 5,312,957  5/1994  Casalnuovo et al. .

FOREIGN PATENT DOCUMENTS 9747633  12/1997  WIPO .

OTHER PUBLICATIONS

Database CAPLUS on STN, Acc. No. 1997:658861, Adger et al., 'Chemoenzymic synthesis of a novel ligand for rhodium–catalyzed asymmetric hydrogenation.' Chem. Commun. (1997), (18), pp. 1713–1714 (abstract), 1997.

Datbase CAPLUS on STN, Acc. No. 1997:1042, Tolstikov et al., 'Chiral organophosphorus ligands derived from the levopimaric acid–maleic anhydride adduct.' Mendeleev Commun. (1996), (6), pp. 215–217 (abstract), 1996.

Database CAPLUS on STN, Acc. No. 1999:94300, Reetz et al., 'New diphosphite ligands for the catalytic asymmetric hydrogenation: the crucial role of conformationally enantiomeric diols.' Angew. Chem., Int. Ed. (1999), 38(1/2), pp. 179–181 (abstract), 1999.

Database CAPLUS on STN, Acc. No. 1998:253209, Zhu et al., 'Highly enantioselective rhodium–catalyzed hydrogenation of dehydroamino acids with new chiral bisphosphinites.' J. Org. Chem. (1998), 63(9), pp. 3133–3136 (abstract), 1998.

Yamamoto, K. et al. (1994) "New Ligands with a Wide Bite Angle. Efficient Catalytic Activity in the Rh(l)–Catalyzed Hydroformylation of Olefins" Chemistry Letters 94(2):189–192.

Yamamoto, K. et al., "Preparation of diphosphinites and hydroformylation of olefins by using them" Chemical Abstracts, vol. 123, No. 9, Aug. 28, 1995, Columbus, Ohio, U.S.; abstract No. 111594z.

Adger, B. et al. (1997) "Chemoenzymatic synthesis of a novel ligand for rhodium–catalysed asymmetric hydrogenation" Journal of the Chemical Society, Chem. Commun. (18):1713–1714.

*Primary Examiner*—Johann Richter
*Assistant Examiner*—Brian J. Davis
*Attorney, Agent, or Firm*—Saliwanchik, Lloyd & Saliwanchik

[57] ABSTRACT

A chiral phosphorus-based ligand, in single enantiomer form, which is capable of complexing a transition metal atom and of acting as a ligand in asymmetric chemical catalysts, which comprises the partial structure

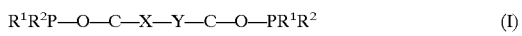

$$R^1R^2P\text{—}O\text{—}C\text{—}X\text{—}Y\text{—}C\text{—}O\text{—}PR^1R^2 \quad \text{(I)}$$

wherein each of X and Y is C or a heteroatom; the C—X—Y—C chain forms part of a linearly-fused bicyclic structure; and either $R^1$ and $R^2$ are each independently H or an organic group of up to 20 carbon atoms, including alkyl, fluoroalkyl, aryl, alkylaryl, alkoxy, aryloxy, and alkylaryloxy, or $PR^1R^2$ is cyclic such that $R^1$ and $R^2$ are covalently linked, optionally with additional substituents.

20 Claims, No Drawings

CHIRAL PHOSPHORUS-BASED LIGANDS

FIELD OF THE INVENTION

This invention relates to chiral phosphorus-based ligands which are useful for asymmetric reactions and especially for asymmetric catalytic reactions when complexed to transition metals.

BACKGROUND OF THE INVENTION

Chiral phosphorus-based ligands are useful as asymmetric catalysts, and many examples are known in the literature. In particular, when complexed with transition metals they have been shown to be effective as catalysts for asymmetric synthesis, for example, the hydrogenation of dehydroanmino acids for the enaitioselective preparation of amino acids.

This has been demonstrated by several groups. For example, Selke et al., J. Mol. Catal. (1986) 213, prepared phosphinites derived from carbohydrates and demonstrated that, when these ligands are complexed with rhodium (I), the resultant catalysts can be used to prepare amino acids, via asymmetric hydrogenation, with excellent enantiomeric excesses.

The use of cliral phosphorus-based compounds as excellent ligands for use in asymmetric synthesis has also been exemplified by the work of RajanBabu et al. Again using phosphinite ligands derived from carbohydrates, this group has demonstrated that when complexed to nickel, the resultant species are effective as catalysts for the enantioselective hydrocyanation of various aromatic vinyl compounds; see U.S. Pat. No. 5,157,335 and U.S. Pat. No. 5,312,957. This same general class of ligands also has displayed excellent enantioselectivities in rhodium-catalyzed hydrogenation reactions; see U.S. Pat. No. 5,510,507 and RajanBabu et al, J.A.C.S. 116:4102 (1994).

Yamamoto et al, Chen. Lett. 94: 189–192(1994), describes an enantiomer of 2,5-bis(diphenylphosplilnoxy) bicyclo[2.2.1]heptane and its use as a ligand in rhodium (I)-catalysed hydroformylation.

An object behind the present invention is to develop alternative chiral scaffolds for the preparation of phosphorus-based ligands. Enantiomerically pure diols can serve as valuable intermediates for the synthesis of a variety of useful phosphorus-based ligands. These can then be used to generate new catalyst systems to carry out various asymmetric reactions.

SUMMARY OF THE INVENTION

Novel chiral phosphorus-based ligands, in single enantiomer form, which are capable of complexing a transition metal atom and of acting as a ligand in asymmetric chemical catalysis, comprise the partial structure $$R^1R^2P-O-C-X-Y-C-O-PR^1R^2 \quad (I)$$

wherein the —C—X—Y—C— chain forms part of a linearly-fused bicyclic structure. X and Y are each independently C or a heteroatom such as N (e.g. at a bridgehead of the bicyclic structure), O or S; each is preferably C. Each P is part of a metal-biniding moiety. $R^1$ and $R^2$ are as defined below, although their precise nature is not a critical feature.

Ligands of the invention have a rigid framework that provides a 9-membered chelate ring with the metal in its complex. The basic framework may then bear additional substitution which may involve further ring fusion but in all cases the framework together with its substituents represents one enantiomer of a chiral species. The respective $PR_1R_2$ groups will usually each be on different rings of the bicyclic system.

In part at least, this invention is based on the discovery that novel, readily accessible chiral enantiomeric diols (5) and (6) can be used to prepare chiral phosphorus-based ligands of the formula (7) or (8); see Reaction Scheme 1, below. These ligands (7 and 8) may be used to form complexes with transition metals (for example rhodium). These complexes have been shown to be effective as catalysts for asymmetric reactions, for example the asymmetric hydrogenation of dehydro amino acids to amino acid derivatives.

DESCRIPTION OF THE INVENTION

Asymmetric reactions of the type to which this invention is particularly applicable include hydroformylation, hydroboration, hydrocyanation and hydrogenation. Suitable substrates for asymmetric hydrogenation include one or more of olefins (C=C), imine (C=N) and ketone (C=O) functionalities. In general, such reactions may be conducted under conditions known to those skilled in the art. In certain cases, particular ligands of the invention may be less suited to certain such reactions; this can readily be determined by those skilled in the art.

The rigid framework in ligands of the invention is provided by a bicyclic framework. This framework is linearly-fused, by which is meant a ring system of the [x.y.0] type; each x and y may be an integer of up to 5, but will typically each be 2, 3 or 4. The most preferred ring system is [3.2.0]. It will generally be carbocyclic (X and Y are each C). If a heteroatom is present, there will usually be no more than one or two, say, N and/or O atoms.

Particular ligands of interest are of formula II, wherein each group R independently represents one or more substituents that are conveniently introduced by a synthetic method such as substitution by a hydrocarbyl group of up to 10 carbon atoms or by a halogen such as bromine. Substitution at the 3- and 5-positions may be particularly accessible, e.g. by the cycloaddition chemistry from cyclopentadiente and a ketene used to provide the bicyclo[3.2.0] heptane framework. While structure II is drawn as only one of the enantiomers, the invention applies equally to the other enantiomer provided always that the ligand is substantially a single enantiomer.

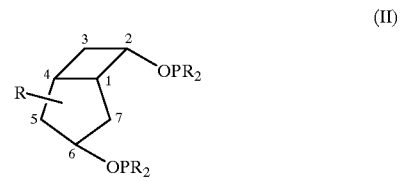

(II)

Various groups $PR^1R^2$ may be used. The preparation of suitable chlorophosphines, from which such groups may be deemed, is described in Perich and Johns, Synthesis (1987), 142; Issleib and Seidel, Chem. Ber. (1959) 92, 2681; Voskuil and Arens, Rec. Trav. Chim. (1963) 82, 302, and Casalnuovo et al, J. Am. Chem. Soc. (1994) 116, 9869.

Ligands of the invention are valuable in asymmetric hydrogenation, particularly as their rhodium complexes. Other metal complexes, e.g. of ligands (II), may be useful; examples of suitable transition metals include rhodium, ruthenium, iridium, palladium, tungsten, molybdenum and nickel. Such complexes may be valuable as catalysts for asymmetric chemical reactions other than asymmetric hydrogenation, such as asymmetric hydroformylation, asymmetric hydroboration, or asymmetric hydrocyanation. The conditions appropriate to the preparation and use of such complexes can readily be determined by those skilled in the art.

Enantiomerically pure (by which is meant substantially free of the opposite enantiomer, e.g. at least 80, 90, 95, 98 or 99% ee) diols (5) and (6) can be obtained through a process beginning with racemic bicyclo[3.2.0]hept-2-en-6-one (1). Compound (1), when treated with N-bromosuccinimide in aqueous acetone, selectively affords racemic bromohydrin (2) in 80% yield, see Grudzinski and Roberts, J. Chem Soc., Perkin Trans. 1, (1975), 1767. Racemic bromohydrin (2) can then be resolved using an efficient biocatalytic method which utilises a yeast-catalysed stereoselective reduction giving a separable mixture of diol (3) and ketone (4). The diol (3) is then debrominated using tributyltin hydride and AIBN in toluene to furnish the (−)-diol (5). Ketone (4) is subjected to debromination using the same conditions (Bu$_3$SnH, AIBN, toluene), followed by reduction of the resultant ketone using sodium borohydride in methanol to yield the (+)-diol (6), as outlined in Scheme 1.

Scheme 1

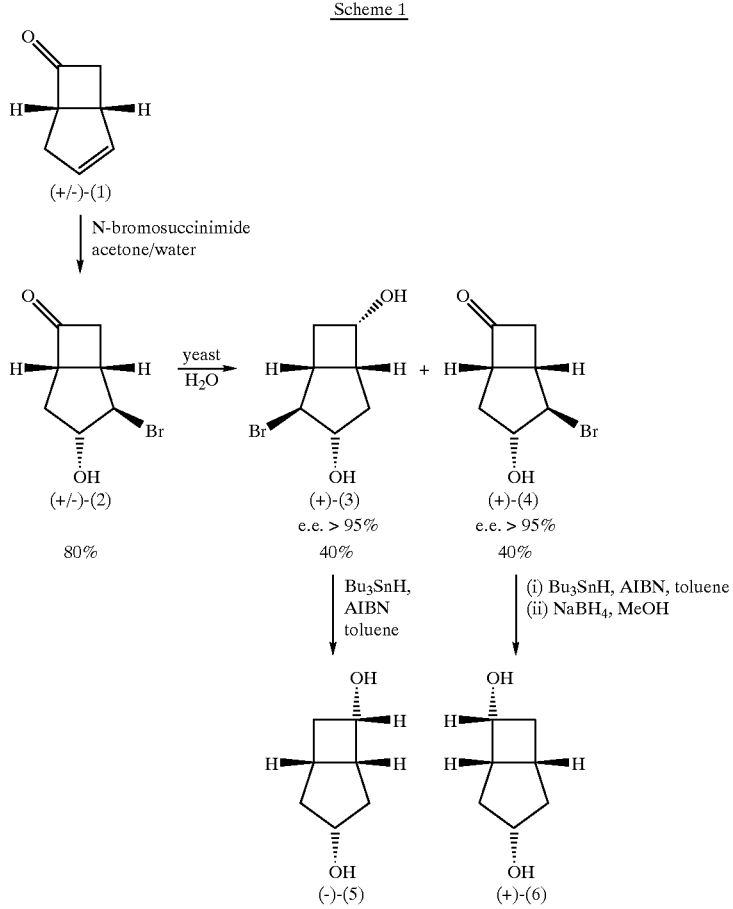

The diol (5) or its enantiomer (6) can then be readily derivatised with reagents of the type ZPR$^1$R$^2$ where Z is any ionisable leaving group, and where R$^1$ and R$^2$ are each independently H or organic groups of up to 20 carbon atoms including alkyl, fluoroalkyl, aryl, alkylaryl, alkoxy, aryloxy, alkylaryloxy and also where ZPR$^1$R$^2$ is cyclic such that R$^1$ and R$^2$ are covalently linked, optionally with additional substituents, to furnish a variety of phosphorus-based ligands of formula (7) or its enantiomer (8) where R$^1$ and R$^2$ are each independently H or organic groups of up to 20 carbon atoms including alkyl, fluoroalkyl, aryl, alkylaryl, alkoxy, aryloxy, alkylaryloxy and also where ZPR$^1$R$^2$ is cyclic such that R$^1$ and R$^2$ are covalently linked, optionally with additional substituents.

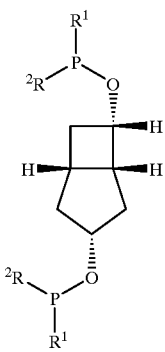

(7)

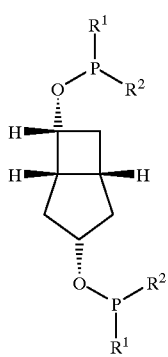

(8)

The ligands of formula (7) or its enantiomer (8) form complexes with transition metals such as rhodium, ruthenium and iridium and these complexes are of use as catalysts for asymmetric reactions. In a specific example, the ligand (7), where $R^1$ and $R^2$ are both Ph, was reacted with [Rh (COD)$_2$]$^+$SO$_3$CF$_3^-$ to give the complex (9). This complex (9) was then used to hydrogenate α-acetamidocinnamic acid in methanol giving N-acetyl phenylalanine in 92.5% e.e. Similarly itaconic acid was hydrogenated with the complex (9) to give 2-methylsuccinic acid in 80.5% e.e.

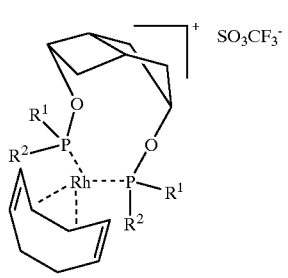

(9)

Other compounds of the invention may be made and used in similar fashion, using modification that will be readily apparent to those skilled in the art.

The following Examples 3 and 4 illustrate diols of the invention Example 10 illustrates ligands of the invention and Example 11 illustrates their use. Other Examples illustrate the preparation of intermediates.

EXAMPLE 1

(1R,2S,3S,5R)-2-Bromo-3-bicyclo[3.2.0]heptan-6-one

To a solution of 20.01 g (180 mmol) of (−)-bicyclo[3.2.0] hept-2-en-6-one in 370 mL of acetone and 105 mL of water was added 42.87 g (240 mmol) of N-bromosuccinimide in portions. The reaction mixture was stirred at room temperature for 20 h. Then 60 mL aqueous sodium metabisulfite (10%) was added to the solution until the initial yellow colour had faded. The acetone was removed in vacuo. The residue was redissolved in 500 mL of ethyl acetate, and washed twice with 50 mL of water and 50 mL of brine. After drying of the organic layer (MgSO$_4$), the solvent was removed in vacuo to leave a solid which was purified by recrystallisation from a mixture of petroleum ether (40/60) and ethyl acetate (2:1 v:v) to give 34.51 g (91%) of the title compound as colorless crystals.

EXAMPLE 2

(1R,3R,5R)-3-Hydroxybicyclo[3.2.0]heptan-6-one

To a solution of 2.01 g (9.8 mmol) of (1R,2,S,3,S,5R)-2-bromo-3-bicyclo[3.2.0]heptan-6-one in 15 mL of dry toluene was added 4.28 g (15 mmol) of tributyltin hydride and 15 mg (0.1 mmol) of AIBN. The reaction mixture was heated to 75° C. for 2 h, allowed to cool to room temperature and then concentrated in vacuo. The tin residue was removed by partitioning between acetonitrile (50 mL) and hexane (35 mL) and re-extracting the acetonitrile layer with hexane (5'35 mL). The solvent was then removed in vacuo and the crude product was purified by chromatography on silica gel with petroleum ether (40/60)—ethyl acetate (1:1 v:v) to give 938 mg (76%) of a colourless solid.

EXAMPLE 3

(1R,3R,5R,6S)-Bicyclo[3.2.0]heptane-3,6-diol

To a solution of 19.33 g (153 mmol) of (1R,3R,5R)-3-hydroxybicyclo[3.2.0]heptan-6-one in 560 mL of dry methanol was added at −78° C. 7.52 g (199 mmol) of sodium borohydride in portions. The reaction mixture was stirred for 2 h and then quenched with 20 mL of saturated ammonium chloride. The mixture was concentrated in vacuo, diluted with 600 mL of ethyl acetate and washed twice with 100 mL of water and 100 mL of brine. The organic layers were dried (MgSO$_4$) and the solvent concentrated in vacuo. The crude product was purified by chromatography on silica gel with petroleum ether (40/60)—ethyl acetate (1:1 v:v). The crude product was recrystallised from hexane to yield 13.70 g (70%) of a colourless solid.

EXAMPLE 4

(−)-(1S,3,S,5S,6R)-bicyclo[3.2.0]heptanedi-3,6-ol

The title compound is prepared as shown in Scheme 1; see also J. Chem. Soc. Chem. Commun. (1997) 18, 1713.

EXAMPLE 5

(1RS,2SR,5RS,6SR)-2,6-Diacetoxy[3.3.0]octane

A solution of 6.6 g (61 mmol) of 1,5-cyclooctadiene in 250 ml of acetic acid was stirred at room temperature for 36 h with 39 g (88 mmol) of Pb(OAc)$_4$ in the presence of 0.4 g (1.8 mmol) of Pd(OAc)$_2$. The mixture was then concentrated in vacuo and the residue was dissolved in 150 mL of ethyl acetate. This solution was extracted twice with 100 mL of water and 100 mL of brine. The organic layer was dried (MgSO$_4$) and the solvent was removed in vacuo. The crude product was purified by chromatography on silica gel with petroleum ether (40/60)—ethyl acetate (4:1) to give 8.68 g (63%) of a colourless solid. See Pérard-Viret and Rassat, Tetrahedron Asymmetry (1994) 5, 1.

EXAMPLE 6

(1RS,2SR,5RS,6SR)-Bicyclo[3.3.0]octanedi-2,6-ol

To a solution of 17.16 g (75 mmol) of (1RS,2SR,5RS, 6SR)-2,6-diacetoxy[3.3.0]octane in 60 mL of methanol was added 53 mL of a solution of potassium hydroxide in methanol (KOH:MeOH 1.33M). The reaction mixture was stirred first at 0° C. in a ice bath for 1 h, and then at room temperature for 2 h and concentrated in vacuo. The residue was dissolved in 200 mL of ethyl acetate, washed with 50 mL of water, dried (MgSO$_4$), and then the solvent was removed in vaco. The crude product was purified by chromatography on silica gel with petroleum ether (40/60)—ethyl acetate (4:1 v:v) to give 10.66 g (85%) of a colourless solid.

EXAMPLE 7

(1R,2S,5R,6S)-bicyclo[3.3.0]octanedi-2,6-ol

To a solution of 7.61 g (53.5 mmol) of the racemic diol of Example 6 in 152 mL of tert-butyl methyl ether was added 53.32 g (375 mmol) of vinyl hexanoate and 1.52 g of Lipase PS (Amano). Thie reaction mixture was stirred at room temperature for 96 h. The reaction was monitored with GC (Chirasil dex CB column ex Chrompack, 25 m' 0.25 mm, 0.25 mm film thickness as trifluoroacetyl derivative of the alcohol intermediates). When the reaction was complete, the enzyme was removed by filtration over a Celite pad. The solvent was then removed, and the excess of vinyl hexanoate was distilled off in vacuo (45° C. at 20 mbar). The residue was diluted with the same volume of pentane, and after standing for 10 days at −24° C. the product crystallised as colourless solid.

EXAMPLE 8

Bis(3,5-dimethyl-4-methoxybenzene) chlorophosphine

A three-neck flask fitted with a condenser and a dropping-funnel was charged with 20.40 g (0.84 mol) of magnesium turnings in 150 mL of THF. To this suspension was added in portions a few mL of a solution of 164.10 g (0.76 mol) of 3,5-dimethyl-4-methoxy-bromobenzene in 200 mL of THF. When the Grignard reaction had started, the rest of the halide solution was added slowly to maintain a gentle reflux. After the addition was completed, the reaction was stirred for another two hours at room temperature. The reaction flask was then cooled to 0° C. in an ice bath and then 60.06 g (0.34 mol) of (Et$_2$N)PCl$_2$ in 100 mL of THF was added via the dropping-funnel. The reaction was first stirred for two hours at 0° C. and then for 30 minutes at 40° C.–50° C. After cooling to room temperature, 900 mL of pentane was added to precipitate the magnesium salts. The salts were filtered off, and the solvent was removed in vacuo. To remove the salts completely, the residue was redissolved in pentane and filtered once more through a celite pad. After removal of the solvent, the residue was dissolved in a Sclilenk flask under nitrogen in 600 mL of pentane and cooled to 0° C. with an ice bath. Dry HCl gas, which was prepared from 115 g (1.05 mol) of conc. H$_2$SO$_4$ and 56.2 g (1.05 mol) of NH$_4$Cl, was passed through this solution for one hour. The salt was then filtered off under nitrogen, and the filter cake was washed for several times with pentane. After removal of the solvent the crude product was distilled to give 32 g (25%) of the chlorophosphinie, bp. 210° C. at 0.2 mbar. $^1$H-NMR (CDCl$_3$, 200 MHz): d 2.16 (s, 6, CH$_3$), 3.70 (s, 3, OCH$_3$), 7.24 (d, 2, $^3J_{PH}$=8.1 Hz). $^{13}$C-NMR (CDCl$_3$, 50 MHz): d 16.06 (s, CH$_3$), 59.48 (s, OCH$_3$), 131.24 (d, C-3, $^3J_{PC}$=8.1 Hz), 132.34 (d, C-2, $^2J_{PC}$=25.6 Hz), 133.87 (d, C-1, $^1J_{PC}$=31.6 Hz), 158.88 (s, C-4). $^{31}$P-NMR(CDCl$_3$, 162 MHz): d 81.85.

EXAMPLE 9

Bis(2-thienyl)chlorophosphine

This chlorophosphine was synthesised in essentially the same way as described in Example 8. From 250 g of 2-bromothiophene, 100 g (56%) of the corresponding chlorophosphine was obtained, bp. 144° C. at 0.1 mbar. The product was obtained as pale yellow oil which solidified at room temperature. $^1$H-NMR (CDCl$_3$, 400 MHz): d 7.19 (ddd, 1, J=5.1 Hz, J=3.4 Hz, J=1.8 Hz); 7.63 (ddd, 1, J=6.4 Hz, J=3.4 Hz, J=1 Hz); 7.78 (dd, 1,J=5.1 Hz, J=1 Hz). $^{13}$C-NMR (CDCl$_3$, 100 MHz): d 127.66 (d, J$_{P,C}$=8.7 Hz), 133.82 (s),135.97 (d, C-2, J$_{PC}$=35.9 Hz) (C-3, C-4); 140.19 (d, C-1, $^1J_{PC}$=46.8 Hz). $^{31}$ P-NMR (CDCl$_3$, 162 MHz): d 51.12.

EXAMPLE 10

Synthesis of a Diphosphinite Ligand (General Procedure)

To a solution of 300 mg (2.34 mmol) of (−)-(1S,3S,5S, 6R)-bicyclo[3.2.0]heptanedi-3,6-ol in 15 mL of dry THF under nitrogen was added 0.50 g (4.91 mmol) of triethylamine. This solution was cooled to 0° C. in an ice bath, and then 4.91 mmol of the chlorophosphine was added dropwise. When the addition was complete, the ice-bath was removed and stirring was continued at ambient temperature for 15 h. The precipitated salt was filtered off through a Celite pad under nitrogen, and then the solvent was removed in vacuo to give the crude product. In order to remove the remaining salts a mixture of diethyl ether/pentane (2:1) was added to the crude ligand, and this was filtered again under nitrogen through a Celite pad. Removal of the solvent gave the diphosphinite ligand as an oil. The ligands prepared by this method were sufficiently pure for in situ catalyst preparations.

Note: Carbons marked in the spectroscopical section with an asterisk are CH$_2$-carbons by DEPT and have not been assigned further.

(1S,3S,5S,6R)-3,6-bis[bis(4-fluorophenyl)phosphinooxy] bicyclo[3.2.0]heptane: Viscous oil. $^{13}$C-NMR (CDCl$_3$, 50 MHz): d 30.16 (s, C-1), 33.80 ('d'), 37.04 ('d'), 40.88 ('d') (C-2*, C-4*, C-7*); 45.43 ('d', C-5); 69.98 ('d', C-3, $^2J_{P,C}$=16.3 Hz); 84.78 ('d', C-6, $^2J_{P,C}$=17.7 Hz); 115.18–116.88 (21 signals, aryl C-1, aryl-C-3); 131.89–133.87 (29 signals, aryl-C-2); 163.54, 163.63, 163.71, 163.77 (4 d, aryl-C-4, $^1J_{PC}$=247 Hz). $^{31}$P-NMR (CDCl$_3$, 162 MHz): δ 103.30 (s), 105.03 (s), J$_{P,P}$≦2 Hz.

[((1S,3S,5S,6R)-3,6-bis[bis(4-fluorphenyl) phosphinooxy]bicyclo[3.2.0]heptane)Rh (COD)]BF$_4$: $^{31}$P-NMR (CDCl$_3$, 162 MHz): δ 105.53, 109.22 (2'dd', J$_{PP}$=10.8, J$_{RhP}$=182 Hz).

(1S,3S,5S,6R)-3,6-bis[bis(4-methoxyphenyl) phospinooxy]bicyclo[3.2.0]-heptane: Viscous oil. $^{31}$P-NNMR (CDCl$_3$, 162 MHz): δ 105.48 (s), 107.51 (s), J$_{PP}$≦2 Hz.

[((1S,3S,5S,6R)-3,6-bis[bis(4-methoxyphenyl) phospinooxy]bicyclo[3.2.0]-heptane) Rh (COD)]BF$_4$: $^{31}$P-NMR (CDCl$_3$, 162 MHz): δ 105.94, 110.61 (2'dd', J$_{PP}$=9.7 Hz, J$_{RhP}$=182 Hz).

(1S,3S,5S,6R)-3,6-bis[bis(4-trifluoromethylphenyl) phosphinooxybicyclo[3.2.0]heptane: Viscous oil: $^{31}$P-NMR (CDCl$_3$, 162 MHz): δ 100.96 (s), 102.35 (s), $J_{PP} \leq 2$ Hz.

[((1S,3S,5S,6R)-3,6-bis[bis(4-trifluoromethylphenyl) phosphinooxybicyclo[3.2.0]heptane) Rh (COD)]BF$_4$: $^{31}$P-NMR (CDCl$_3$, 162 MHz): δ96.29, 113.07 (2 'dd', $J_{RhP}$=20.6 Hz, $J_{PP}$=176 Hz).

(1S,3S,5S,6R)-3,6-bis[bis(2,3-dimethyl-4-methoxyphenyl)phosphinooxy-bicyclol[3.2.0]heptane): Viscous oil. $^{31}$P-NMR (CDCl$_3$, 162 MHz): δ 105.43 (s), 107.70 (s), $J_{PP} \leq 2$ Hz.

[((1S,3S,5S,6R)-3,6-bis[bis(2,3-dimethyl-4-methoxyphenyl)phosphinooxy]-bicyclo[3.2.0]heptane) Rh(COD)]BF$_4$: $^{31}$P-NMR (CDCl$_3$, 162 MHz): δ 105.53, 109.22 (2 'dd', $J_{PP}$=10.8 Hz, $J_{RhP}$=182 Hz).

(1S,3S,5S,6R)-3,6-bis[bis(cyclohexyl)phosphinooxy] bicyclol[3.2.0]heptane: $^{31}$P-NMR (CDCl$_3$, 162 MHz): δ 147.36 (s), 150.51 (s), $J_{PP} \leq 2$ Hz.

The Rh(COD)BF$_4$ complex of this compound may be made by analogy with the procedures described above.

EXAMPLE 11

Asymmetric Hydrogenations

To 0.01 mmol of the diphosphinite ligand, e.g. derived from the diol of Example 3, was added in a Schlenk flask under nitrogen 5 mL of degassed methanol and 0.011 mmol of [(COD)$_2$Rh]BF$_4$. The reaction mixture was stirred at room temperature until everything was dissolved.

To the liner of a 50 ml hydrogenation bomb was charged 1 mmol of the substrate and a magnetic stirrer bar. The bomb was then assembled and flushed three times with hydrogen at 1380 kPa (200 psi). The hydrogen was vented, and then the solution of the in situ formed catalyst was added through the solvent port. The hydrogenation was performed at room temperature and 1380 kPa (200 psi) hydrogen pressure, and was complete after 3 hours in all cases (reaction control by GC). The ee values of the hydrogenation products were determined either by chiral HPLC or by chiral GC, and the results are tabulated below, for the substrates α-acetamidocinnamic acid and methyl 2-acetamideacrylate. The "ligand" shows only the varying group of that material.

| Ligand | Substrate: a-acetamido-cinnamic acid | Substrate: methyl 2-acetamido-acrylate |
| --- | --- | --- |
| 4-fluorophenyl | 91.1 ± 0.7% (R) | 70.4 ± 2.2% (S) |
| 4-(trifluoromethyl) phenyl | 66.7 ± 5.9% (R) | 66.4 ± 0.4% (A) |
| 4-methoxy-3,5-dimethylphenyl | 83.9 ± 3.4% (R) | 71.9 ± 2.9% (S) |
| 4-methoxyphenyl | 90.3 ± 1.7% (R) | 67.7 ± 1% (S) |
| 2-thienyl | 87.5 ± 0.1% (R) | 71.1 (S) |
| cyclohexyl | 55.2 ± 0.5% (S) | 25.7 ± 1.6% (R) |

What is claimed is:

1. A chiral phosphorus-based ligand, in single enantiomer form, which is capable of complexing a transition metal atom and of acting as a ligand in asymmetric chemical catalysis, which comprises the structure $$R^1R^2P\text{—}O\text{—}C\text{—}X\text{—}Y\text{—}C\text{—}O\text{—}PR^1R^2 \quad (I)$$

wherein each of X and Y is C or a heteroatom selected from the group consisting of N, O and S; the C—X—Y—C chain forms part of a linearly-fused bicyclic structure; and either R$^1$ and R$^2$ are each independently H, alkyl, fluoroalkyl, aryl, alkylaryl, alkoxy, aryloxy, or alkylaryloxy or PR$^1$R$^2$ is cyclic such that R$^1$ and R$^2$ are covalently linked.

2. The ligand, according to claim 1, wherein the PR$^1$R$^2$ groups are each part of phosphinite substituents borne on different rings of a bicyclic structure.

3. The ligand, according to claim 2, that comprises a bicyclo[3,2,0]heptane structure.

4. The ligand, according to claim 1, wherein X and Y are each C.

5. The ligand, according to claim 1, of formula (7) or its enantiomer (8)

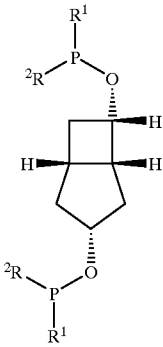

(7)

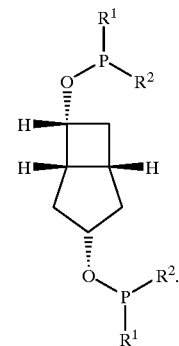

(8)

6. A transition metal complex of a chiral phosphorus-based ligand, wherein said ligand is in single enantiomer form and is capable of complexing a transition metal atom and of acting as a ligand in asymmetric chemical catalysis and comprises the structure $$R^1R^2P\text{—}O\text{—}C\text{—}X\text{—}Y\text{—}C\text{—}O\text{—}PR^1R^2 \quad (I)$$

wherein each of X and Y is C or a heteroatom selected from the group consisting of N, O, and S; the C—X—Y—C chain forms part of a linearly-fused bicyclic structure; and either R$^1$ and R$^2$ are each independently H, alkyl, fluoroalkyl, aryl, alkylaryl, alkoxy, aryloxy, or alkylaryloxy or PR$^1$R$^2$ is cyclic such that R$^1$ and R$^2$ are covalently linked.

7. The complex, according to claim 6, wherein the metal is selected from the group consisting of rhodium, ruthenium, iridium, palladium, tungsten, molybdenum, and nickel.

8. The complex, according to claim 7, wherein in said ligand, X and Y are each C, and the metal is selected from the group consisting of rhodium, ruthenium, and iridium.

9. The single enantiomer diol (−)-(5) or (+)-(6)

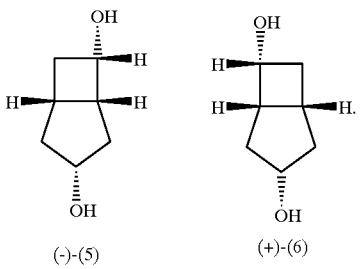

(−)-(5)   (+)-(6)

10. A process for the preparation of a ligand of claim 5 which comprises the reaction of a diol, (−)-(5) or (+)-(6), with a compound of formula $ZPR^1R^2$ where Z is any ionisable leaving group, and $R^1$ and $R^2$ are each independently H alkyl, fluoroaryl, aryl, alkylaryl, alkoxy, aryloxy, or alkylaryloxy, or $PR^1R^2$ is cyclic such that $R^1$ and $R^2$ are covalently linked.

11. An improvement in an asymmetric reaction method, wherein said improvement comprises the addition of a ligand according to claim 1.

12. The method, according to claim 11, wherein said asymmetric reaction is an asymmetric hydrogenation reaction.

13. The method, according to claim 12, wherein the substrate that is hydrogenated comprises an olefin (C=C), an imine (C=N), or a ketone (C=O) functionality.

14. The method, according to claim 11, wherein said asymmetric method is asymmetric hydroformylation, asymmetric hydroboration, or asymmetric drocyanation.

15. An improvement in an asymmetric reaction method, wherein said improvement comprises the addition of a ligand according to claim 6.

16. The method, according to claim 15, wherein said asymmetric reaction is an asymmetric hydrogenation reaction.

17. The method, according to claim 16, wherein the substrate that is hydrogenated comprises an olefin (C=C), an imine (C=N), or a ketone (C=O) functionality.

18. The method, according to claim 15, wherein said asymmetric method is asymmetric hydroformylation, asymmetric hydroboration, or asymmetric hydrocyanation.

19. A method of catalyzing an asymmetric reaction comprising the addition of a catalytic ligand according to claim 1 to a substrate containing a prochiral functionality wherein said reaction produces a product with at least one new chiral center.

20. A method of catalyzing an asymmetric reaction comprising the addition of a catalytic ligand according to claim 7 to a substrate containing a prochiral functionality wherein said reaction produces a product with at least one new chiral center.

* * * * *

UNITED STATES PATENT AND TRADEMARK OFFICE
CERTIFICATE OF CORRECTION

PATENT NO. : 6,156,935
DATED : December 5, 2000
INVENTOR(S) : Stanley M. Roberts, et. al.

It is certified that error appears in the above-identified patent and that said Letters Patent is hereby corrected as shown below:

Column 14, line 3: "drocyanation" should read --hydrocyanation--.

Signed and Sealed this

First Day of May, 2001

Attest:

NICHOLAS P. GODICI

Attesting Officer      Acting Director of the United States Patent and Trademark Office